United States Patent [19]

Gifford, III et al.

[11] Patent Number: 5,071,425
[45] Date of Patent: Dec. 10, 1991

[54] ATHERECTOMY CATHETER AND METHOD OF FORMING THE SAME

[75] Inventors: Hanson S. Gifford, III, Palo Alto; Richard L. Mueller, Mountain View, both of Calif.

[73] Assignee: Devices for Vascular Intervention, Inc., Redwood City, Calif.

[21] Appl. No.: 711,506

[22] Filed: Jun. 3, 1991

Related U.S. Application Data

[63] Continuation of Ser. No. 449,014, Dec. 11, 1989, abandoned, which is a continuation-in-part of Ser. No. 243,397, Sep. 12, 1988, abandoned.

[51] Int. Cl.⁵ ................. A61B 17/22; A61M 29/02
[52] U.S. Cl. ........................... 606/159; 156/86; 156/294; 264/573; 264/342 R; 264/516
[58] Field of Search ............ 606/159, 170, 171, 194; 604/22; 156/86, 85, 294; 264/573, 342 R, 516, 512, DIG. 71

[56] References Cited

U.S. PATENT DOCUMENTS

| | | | |
|---|---|---|---|
| 3,528,869 | 9/1970 | Dereniuk | 264/573 X |
| 4,213,461 | 7/1980 | Pevsner | 604/96 |
| 4,248,236 | 2/1981 | Linder | 606/108 X |
| 4,251,305 | 2/1981 | Becker et al. | 604/103 X |
| 4,323,071 | 4/1982 | Simpson et al. | |
| 4,411,055 | 10/1983 | Simpson et al. | |
| 4,627,436 | 12/1986 | Leckrone | |
| 4,638,805 | 1/1987 | Powell | 604/97 X |
| 4,669,469 | 6/1987 | Gifford et al. | 606/159 |
| 4,685,458 | 8/1987 | Leckrone | |
| 4,715,378 | 12/1987 | Pope et al. | 606/194 |
| 4,790,315 | 12/1988 | Mueller et al. | 604/96 X |

FOREIGN PATENT DOCUMENTS

| | | |
|---|---|---|
| 0163502 | 12/1985 | European Pat. Off. |
| 0213750 | 3/1987 | European Pat. Off. |
| 0299158 | 1/1989 | European Pat. Off. |
| 0311427 | 4/1989 | European Pat. Off. |
| 2740063 | 3/1978 | Fed. Rep. of Germany |

OTHER PUBLICATIONS

Sales Sheet 132-8/86-LIS.

Primary Examiner—Michael H. Thaler
Attorney, Agent, or Firm—Townsend and Townsend

[57] ABSTRACT

An atherectomy device includes a transparent lumen for providing inflation medium to an inflatable balloon. A dual lumen flexible tube includes an opaque flexible torque member in a first lumen, while the second lumen serves as an inflation lumen. The distal end of the inflation lumen is expanded to define the balloon, and no seals are needed between the balloon and the inflation lumen.

15 Claims, 2 Drawing Sheets

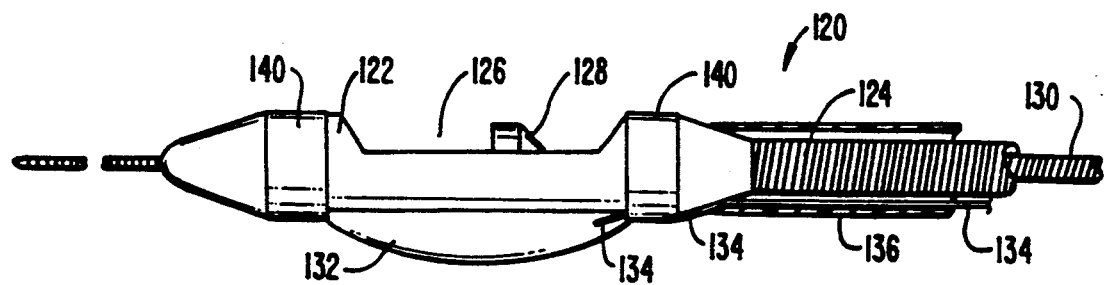
FIG._1. PRIOR ART
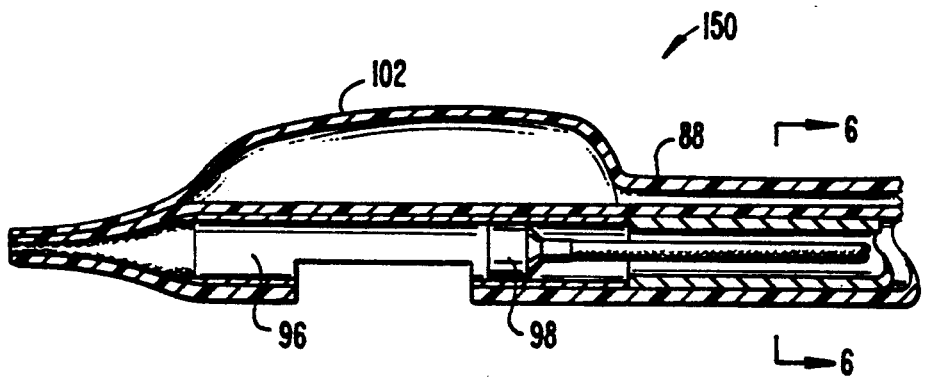
FIG._5.
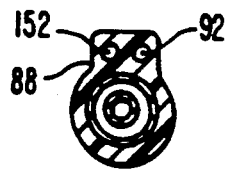
FIG._6.
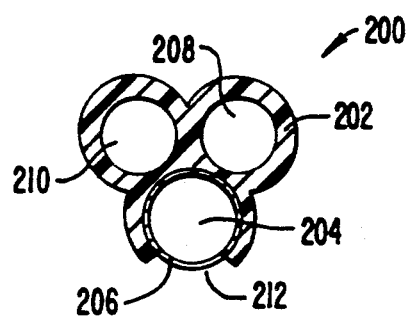
FIG._7.

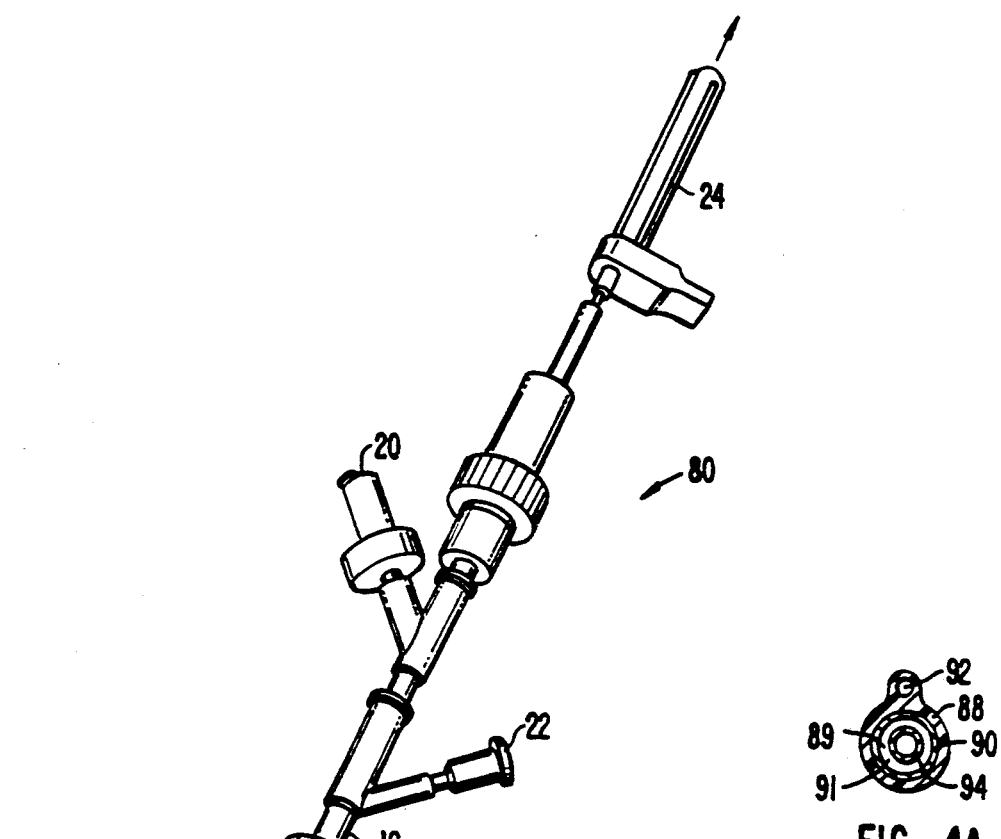
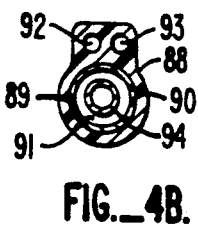
FIG._4A.
FIG._4B.
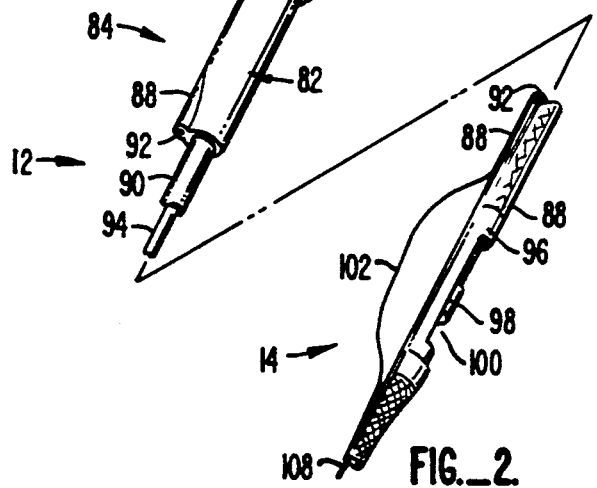
FIG._2.
FIG._3.

ATHERECTOMY CATHETER AND METHOD OF FORMING THE SAME

This is a continuation of application Ser. No. 07/449,014, filed Dec. 11, 1989, now abandoned which is a continuation-in-part of application Ser. No. 07/243,397, filed on Sept. 12, 1988, now abandoned, the disclosure of which is incorporated herein by reference.

BACKGROUND OF THE INVENTION

1. Field of the Invention

The present invention relates generally to the construction of atherectomy catheters for removing atheromas from a patient's arteries. In particular, the present invention relates to atherectomy devices using an inflatable balloon for effecting contact between an interventional implement and the atheroma.

Atherosclerosis is a condition characterized by fatty deposits (atheromas) in the intimal lining of a patient's arteries. Atherosclerosis can have many manifestations, including angina, hypertension, myocardial infarction, strokes, and the like. Initially, the atheromas deposited in the blood vessels remain relatively soft and tractable. Over time, however, the atheromas become calcified and hardened.

Atherectomy is a procedure which has been developed for removing atheromas from the vascular system, usually before substantial calcification has occurred. Atherectomy procedures utilize special catheters having a severing instrument located at a distal end thereof and, usually, an inflatable balloon located opposite the severing instrument. The catheter is positioned within the vascular system so that the severing instrument lies adjacent the atheroma, and the balloon is inflated to bring the severing instrument into close proximity with the atheroma. The severing instrument is then actuated to excise the atheroma, and the severed material captured to prevent the release of emboli.

The severing instrument on the atherectomy catheter can take a variety of forms, including fixed blades, (requiring movement of the entire catheter to effect cutting) and movable blades which can be actuated without movement of the catheter as a whole. Of particular interest to the present invention are atherectomy catheters having rotatable cutting blades which can be advanced across an aperture formed in a housing. The balloon is mounted on the housing so that the atheroma may be urged into the aperture with the cutting element being advanced to sever the atheroma. The use of the invention, however, is not limited to such cutting blades and applies to catheters having a wide variety of interventional implements mounted in a distal housing.

Heretofore, atherectomy devices have suffered from deficiencies in the manner in which inflation medium is supplied to the inflatable balloon. Atherectomy catheters generally require a torqueable shaft within the catheter body which allows the cutting head to be rotatably aligned with the atheroma after the catheter has been placed within the vascular system. Such torqueable shafts are typically formed from braided metal or other opaque materials which prevent viewing of the interior of the catheter. Thus, balloon inflation supply tubes which are inside the shaft are not visible, preventing examination for air bubbles. Air bubbles within the inflation medium are, of course, unacceptable as they could lead to air emboli should the inflatable balloon burst.

Additionally, the atherectomy catheters have suffered from problems in the sealing and joining of the inflation medium supply tubes to the inflatable balloon. As most atherectomy devices employ inflatable balloons which are separate from the tube or other member supplying inflation medium, a potential failure point is found at the junction between the inflation medium supply tube and the balloon. Moreover, the mechanical attachment of the balloon to the housing can be problematic.

Referring to FIG. 1 (prior art), the construction of an exemplary prior atherectomy catheter 120 is illustrated. The atherectomy catheter is of the type described in European Patent Application 163 502, the disclosure of which is incorporated herein by reference. Atherectomy catheter 120 includes a distal housing 122 secured to the distal end of a torqueable shaft 124. The housing 122 is axially and rotationally positioned within a patient's vascular system solely by manipulation of the proximal end of the catheter (not illustrated) with the torqueable shaft 124 acting to transmit all such motion.

The housing 122 has an elongate cutout 126 on one side thereof, and a rotatable cutting blade 128 is attached to the distal end of a drive cable 130. In use, the cutout 126 is urged against a region of atheroma by an inflatable balloon 132. Once the atheroma is within the cutout, blade 128 is driven using cable 130 to sever at least a portion of the atheroma.

Balloon 132 is inflated by an inflation tube 134 which is located on the outside of torqueable shaft 124 beneath a sheath 136. The sheath 136 will normally be constricted about the torqueable shaft in order to hold inflation tube 134 in place about the torqueable shaft 124.

Although a feasible construction, such placement of the inflation tube and inflatable balloon has several disadvantages. First, the small diameter of inflation tube 134 obscures the interior of the tube, masking any air bubbles which may be present. Second, the sheath 116 can cause constriction of the inflation tube 134, which can interfere with inflation of the balloon 132 under certain types of bending. Third, passage of the inflation tube 134 into the balloon is problematic. The tube 134 must pass beneath a clamping ring 140 which (together with a second clamping ring 140) holds the inflatable balloon 132 in place. The use of such clamping rings increases the likelihood that the inflation tube 134 may be constricted and further obscures visual examination of the tub for bubbles. Finally, use of the clamping rings 140 to secure the balloon 132 is problematic. The balloon 132 is held only at the ends, and the middle of the balloon has a tendency to roll away from the housing rendering positioning of the cutting blade 128 difficult. In alternate constructions (not illustrated), the balloon is attached to the housing by adhesives. Such adhesive attachment, however, can damage the fragile, thin-walled balloon material.

For the above reasons, it would be desirable to provide atherectomy and other interventional catheters where the entire balloon inflation system within the device is visible to the user while the device is being primed with inflation medium. Such visibility will allow the user to check for air bubbles which would endanger the patient should the inflatable balloon on the device burst during use. Additionally, it would be desirable to provide atherectomy devices having improved connections between the inflatable balloon and the tube or lumen supplying inflation medium through the length of the catheter. It would be particularly desirable if the balloon could be formed integrally (without joints) with the inflation medium supply tube or lumen. Finally, it would be desirable to provide such atherectomy catheters where the balloon were attached to the housing along its entire length so that the tendency of the balloon to roll away from the housing is minimized.

2. Description of the Background Art

U.S. Pat. Nos. 4,323,071 and 4,411,055 disclose balloon-tipped angioplasty catheters formed from inner and outer coaxial tube members. The outer coaxial tube defines the inflation balloon at its distal end and serves to carry inflation medium along the length of the catheter. U.S. Pat. Nos. 4,627,436 and 4,685,458 describe atherectomy devices which utilizes a fixed blade to sever atheroma. A lumen within the device carries inflation medium to a balloon located opposite the blade at the distal end of the device. U.S. Pat. No. 4,669,469 describes a single lumen atherectomy device where both a cutter cable and inflation medium pass through the lumen. The lumen is connected to the interior of an inflation balloon and the cutter cable is sealed by an O-ring. EPO 163 502 discloses an atherectomy device including a small diameter, discrete tube passing through a central lumen for providing inflation medium to an inflatable balloon. American Edwards Laboratories, Santa Ana, Calif., sells a balloon-tipped catheter having discrete inflation and vent lumens extending from the entire catheter length, as illustrated in sales sheet 132-8/86-LIS.

SUMMARY OF THE INVENTION

According to the present invention, a vascular catheter comprises a substantially transparent flexible tube having proximal and distal ends and at least two lumens extending therebetween. A housing containing an interventional element is disposed in a first lumen at the distal end of the flexible tube and connected to an opaque torque member which extends through the remaining portion of said first lumen. An inflation balloon is formed as an expanded region of the second lumen and is disposed adjacent to the housing so that, when inflated inside a blood vessel, the housing will be urged against an atheroma. The remainder of the second lumen has a reduced diameter compared to the balloon region and serves as an inflation lumen extending from the proximal end to the distal end of the flexible tube. The resulting inflation lumen and balloon are substantially transparent and unobstructed along their entire length so that the user can observe any air bubbles which may be present while priming the catheter with inflation medium.

Such construction provides an inflation balloon and lumen which are integrally formed from one lumen of a single flexible tube. The balloon is conveniently formed by thermal expansion of the distal end of the second (inflation) lumen, with the remaining length of the lumen then providing a connection (inflation lumen) for the inflation medium. The opaque torque tube is disposed in the second lumen, with the second lumen normally being constricted over both the torque tube and the housing to provide strong bonding. This construction has particular advantages since there are no seals or joints required between the inflation balloon and the inflation medium supply lumen. Moreover, the inflation balloon is firmly attached to the cutter housing which is disposed in the second lumen with the torque tube. Thus, the inflation balloon will remain properly aligned with the housing at all times.

BRIEF DESCRIPTION OF THE DRAWINGS

FIG. 1 is a side elevational view of a prior art atherectomy device.

FIG. 2 is a perspective view of a catheter constructed in accordance with the principles of the present invention.

FIG. 3 is an elevational view of the distal end of the catheter of FIG. 2, shown in section.

FIG. 4A is a cross-sectional view taken along line 4—4 of FIG. 3.

FIG. 4B is similar to FIG. 4A, but illustrates a third lumen in the catheter.

FIG. 5 is an elevational view of the distal end of an alternate embodiment of a catheter constructed in accordance with the principles of the present invention.

FIG. 6 is a cross-sectional view taken along line 6—6 of FIG. 5.

FIG. 7 is a cross-sectional view of a second alternate construction of an atherectomy catheter constructed in accordance with the principles of the present invention.

DESCRIPTION OF THE SPECIFIC EMBODIMENTS

Referring to FIGS. 2-4, an atherectomy catheter 80 includes a proximal end 12 and a distal end 14. A manifold connector 16 at the proximal end 12 includes a conventional rotatable fitting 18 for joining the manifold 16 to a flexible catheter body 82. A balloon port 22 and flush port 20 are provided and connected to the catheter body 82, as described in greater detail hereinafter. A driver connection 24 is attached to a cutter torque cable 94, and is able to rotate and axially translate the cable, typically using a motor drive unit (not illustrated) such as that described in U.S. Pat. No. 4,771,774, the disclosure of which is incorporated herein by reference. The design and construction of the manifold connector 16 is conventional and need not be described further.

General considerations relating to the design and construction of atherectomy catheters are described in copending applications Ser. No. 07/298,846 now U.S. Pat. No. 4,979,951 and Ser. No. 07/405,906, pending the disclosures of which are incorporated herein by reference. The constructions of the present invention may also find use with balloon-assisted vascular incision devices as described in copending application Ser. No. 142,382, now U.S. Pat. No. 5,053,044 the disclosure of which is incorporated herein by reference.

The catheter body 82 is that portion of the atherectomy catheter 80 which extends from the manifold housing 16 to a cutter housing 96 at the distal end. The catheter body 82 includes a flexible torque member 90 which is fixedly attached to the rotation of manifold housing 16 so that rotation of the rotator will result in rotation of the catheter body 82 along its entire length, resulting in rotation of the cutter housing 96.

The flexible torque member 90 will normally be a braided metal cable, typically a stainless steel braided cable, as described in co-pending application Ser. No. 07/298,846, the disclosure of which has previously been incorporated herein by reference. It is important that the flexible torque member be highly flexible, yet remain capable of transmitting torque along its entire length with a minimal loss of transmission efficiency. The diameter of the flexible torque member 90 will vary depending on the intended application of the catheter 80, generally being in the range from about 1 mm to 4 mm, usually being in the range from about 2 to 4 mm for peripheral arteries and in the range from about 1 to 2 mm for coronary arteries.

The cutter torque cable 94 extends through the lumen of flexible torque member 90, having a diameter in the range from about 0.4 mm to 1.5 mm, usually being in the range from about 0.5 mm to 1.0 mm. Conveniently, the cutter torque cable 94 may be formed from multi-stranded stainless steel wire. If it is desired to pass a steerable guidewire through the center, the cable 94 should be formed into a tube, typically a braided tube, such as a stainless steel braid, coated with a plastic, such as a urethane.

A first annular lumen 91 is formed between the inside wall of flexible torque member 90 and the outside of the cutter torque cable 94. The annular lumen 91 is connected with the flush port 20 on manifold housing 16. During use of the atherectomy catheter 80, the flush port 20 will be connected to a suitable source of flushing solution.

Cutter housing 96 is generally a hollow cylindrical structure which is fixedly attached to the distal end of flexible torque member 90, thus forming an extension thereof. The cutter housing 96 will usually be a rigid structure, typically formed from stainless steel or other surgically acceptable metals, but may also be a flexible structure as described in U.S. Pat. No. 4,781,186, the disclosure of which is incorporated herein by reference. An elongate aperture 100 is formed on a one side of the cutter housing 96, and a cup-shaped cutting blade 98 is rotatably mounted within the interior thereof. The length of the cutter housing is not critical, typically being in the range from about 10 mm to 50 mm, usually being in the range from 12 mm to 40 mm. The elongate aperture 100 will typically have a length in the range from about 5 mm to 45 mm and a width in the range from about 1 mm to 4 mm. The cutting blade 98 is attached to the distal end of cutter torque cable 94, so that the blade 98 may be rotated and axially translated by manipulation of the cutter blade attachment member 24. Conveniently, motorized means for rotating and translating the cutter blade may be provided, as described in co-pending U.S. Pat. No. 4,771,774, previously incorporated herein by reference.

Although a cup-shaped cutting blade is illustrated, it will be appreciated that a variety of other rotatable interventional elements may be substituted. For example, the use of helical cutting blades is described in U.S. patent application Ser. No. 07/405,906, the disclosure of which has previously been incorporated herein by reference. Other interventional implements, such as drills, may also find use.

An inflatable balloon 102 is located on the side opposite to the aperture 100 on cutter housing 96. The inflatable balloon 102 will be transparent and be formed integrally as an expanded portion of a lumen of a flexible tube which is part of the catheter body, as described below. Typically, the balloon will have a width, when fully inflated, of approximately 1 mm to 6 mm, more usually about 2 mm to 4 mm.

A flexible open-ended tip 106 is attached to the distal end of cutter housing 96, forming a continuous interior volume therewith. The interior volume of the tip 106 is capable of receiving and retaining atheroma material which is severed by blade 98 as it is brought forward in the housing 96. The flexible tip 106 also facilitates positioning the catheter 80 over a conventional guidewire (not illustrated) in the vascular system. The flexible tip 106 is conveniently formed from a braided material typically braided stainless steel, and is attached to the cutter housing 96 by conventional means.

Catheter body 82 extends from proximal end 12 to distal end 14 of the atherectomy catheter 80. The catheter body 82 is formed from a multiple lumen flexible tube 88 including at least a first lumen 89 and a second lumen 92 (with a third lumen 93 illustrated in FIG. 4B). The flexible torque member 90 is disposed in the first lumen 89, while the second lumen 92 defines both an inflation lumen or conduit and the inflatable balloon 102, as will be described in more detail hereinafter. Cutter torque cable 94 passes through the interior of flexible torque member 90, and the construction of both the flexible torque member 90 and cutter torque cable 94 are described above. The flexible tube 88 will be composed of a translucent thermoplastic material, such as a heat-shrinkable polyolefin, preferably being a surlyn or polyethylene.

The initial sizes of the two lumens 89 and 92 are not critical so long as they may be manipulated to assume the desired final dimensions, as described below. Initially, the first lumen 89 will be expanded using hot air and internal pressure. The flexible torque member 90 may then be inserted into the expanded lumen 89, and the lumen further heated (without internal pressure) in order to constrict the tube 88 about the flexible torque member. Conveniently, a space maintainer (not illustrated), such as a teflon rod, may be inserted in the second lumen while the flexible torque member 90 is being inserted into the first lumen 89. Conveniently, the teflon rod will have the desired diameter for the final inflation lumen so that such diameter is simultaneously achieved, while the flexible torque member 90 is being inserted. The diameter of the first lumen will depend on the outer diameter of the flexible torque member 90, typically being between about 1 mm and 4 mm, more typically being between about 1.5 mm and 3 mm. The inflation lumen 92 will have a diameter in the range from about 0.3 mm to 1.0 mm, more usually being in the range from about 0.4 mm to 0.7 mm. An optional third lumen 93 may be provided for receiving a steerable guidewire (not illustrated) to allow positioning of the catheter in a conventional manner. Additional lumens (not illustrated) may be provided in the flexible tube 88 as desired for other purposes.

The distal end 86 of the catheter 80 includes the cutter housing 96 which is fixedly attached to the distal end of the flexible torque member 90. The first lumen 89 will be constricted about the housing 96 simultaneous with constriction about the torque member 90.

A cutter member 98 is attached to the distal end of cutter torque cable 94, and is able to be rotated and axially translated past aperture 100 formed in the cutter housing 96. The portion of flexible tube 88 which covers the aperture 100 after constriction will typically be cut away to fully expose the interior of the housing 96. Usually, an adhesive will be applied around the window opening to hold the entire balloon structure in place on the housing 96.

Balloon 102 is formed by expanding the inflation lumen 92 adjacent to the cutter housing 96. Conveniently, expansion is achieved using hot air at an elevated pressure, and the final dimensions may be achieved by inserting an appropriate spacer block and reheating the material to provide shrinkage. The dimensions of the balloon 102 will be generally the same as described hereinbefore.

The flexible tip 106 is attached to the distal end of cutter housing 96, as described previously. The distal end of flexible tube 88 is constricted about the flexible tip 106 by heating, and a balloon vent may be provided by inserting a flexible tube 108, typically a fused silica tube, through the lumen 92 prior to constriction. Alternatively, the tube 108 can be bonded to the flexible tube 88 with a flexible adhesive. After constriction, the flexible tip 106, flexible vent tube 108 and constricted tubing 88 form a compliant tip for the catheter which facilitates positioning the catheter as described above. The flexible vent tube 108 will typically have an inner diameter in the range from about 0.05 mm to 0.3 mm.

Referring to FIGS. 5 and 6, an alternate venting system for an atherectomy catheter constructed in accordance with the principles of the present invention will be described. The catheter 150 (only the distal portion of which is illustrated) includes housing 96, flexible tube 88, balloon 102, and cutting blade 98, all essentially as described previously in connection with FIGS. 2-4. The primary difference with the previously-described embodiment is in the vent system where a vent lumen 152 is provided in the flexible tube 88 in addition to inflation lumen 92. The balloon 102 is formed by removing the material between lumens 92 and 152 at the distal tip of the tube 88 and expanding that region into the balloon, with heat, as described previously. The portion of the lumens 92 and 152 which remains at the end of the tube 88 can then be sealed, either by heat or with an adhesive. Venting of balloon 102 can then be effected through lumen 152 simultaneously with inflation through lumen 92.

Referring now to FIG. 7, FIG. 7 is a cross sectional view of a second alternate construction of an atherectomy catheter constructed in accordance with the principles of the present invention will be described. FIG. 7 is a cross-sectional view of a catheter 200 comprising a single flexible tube 202 having three lumens formed therein. The first lumen 204 has been expanded to hold a housing 206 similar to the previously-described housing 96. The second and third lumens 208 and 210 have both been expanded to form inflation balloons, where unexpanded portions of the lumens serve as inflation lumens. The symmetric positioning of two inflation balloons opposite the cutting aperture 212 is advantageous since it can position the housing 206 more stably within the blood vessel.

Although the foregoing invention has been described in some detail by way of illustration and example for purposes of clarity of understanding, it will be obvious that certain changes and modifications may be practiced within the scope of the appended claims.

What is claimed is:

1. A vascular catheter comprising:
    a substantially transparent flexible tube having at least a first lumen and a second lumen extending from a proximal end to a distal end thereof;
    a flexible torque member extending within a proximal portion of a first of the lumens, said torque member having an open interior;
    a housing disposed within the distal end of the first lumen and joined to the flexible torque member;
    means for removing atheroma within said housing;
    wherein the first lumen is constructed about both the flexible torque member and the housing and wherein the second lumen is enlarged at its distal end to form an inflatable balloon adjacent the housing, and wherein the first lumen of the flexible tube extends over the housing at least as far as the balloon extends adjacent the housing.

2. A vascular catheter as in claim 1, wherein an axially-elongated aperture is formed in the housing and first lumen to expose the means for removing.

3. A vascular catheter as in claim 1, wherein said housing includes an axially elongated aperture and said removing means comprises a rotatable blade mounted within the housing and a flexible cable attached to the blade, said cable being capable of rotating and axially translating the blade past the elongated aperture.

4. A vascular catheter as in claim 3, wherein the inflatable balloon is disposed on the side of the housing opposite the aperture.

5. A vascular catheter as in claim 1, wherein the flexible torque member is a braided tube having a diameter from about 1 mm to 4 mm.

6. A vascular catheter as in claim 1, further including at least a third lumen formed in the substantially transparent tube connecting the interior of the inflatable balloon to a proximal vent, whereby air within the balloon and the second lumen may be bled during inflation of the balloon with an incompressible fluid.

7. A vascular catheter as in claim 1, wherein the flexible tube includes at least a third lumen capable of receiving a steerable guidewire.

8. A vascular catheter as in claim 1, wherein the housing occupies from 10 to 50 mm of the distal end of the first lumen while the flexible torque member occupies the remaining length of the first lumen.

9. A vascular catheter as in claim 1, wherein the flexible tube includes at least a third lumen, wherein the third lumen is enlarged at its distal end to form a second inflatable balloon adjacent the housing.

10. A method for forming a vascular catheter, said method comprising:
    constricting a first lumen of a substantially transparent flexible tube having at least a first and a second lumen about a flexible torque member and a housing joined to a distal end of the flexible torque member; and
    expanding distal region of the second lumen proximate the housing to form an inflatable balloon.

11. A method as in claim 10, wherein the flexible tube is composed of a thermoplastic and the first lumen is constructed by heating.

12. A method as in claim 10, wherein the distal region of the second lumen is expanded by heating and applying internal pressure to the interior thereof.

13. A method as in claim 10, further comprising:
    constructing a proximal region of the second lumen to a preselected diameter to form an inflation lumen for the balloon.

14. A method as in claim 13, wherein the proximal region is constricted about a rod to maintain the preselected diameter.

15. A method as in claim 10, further comprising expanding a distal region of a third lumen proximate the housing to form a second inflatable balloon.

* * * * *